United States Patent
Mulumudi et al.

(10) Patent No.: US 8,926,684 B2
(45) Date of Patent: *Jan. 6, 2015

(54) ENDOPROSTHESIS STENT DELIVERY SYSTEM AND METHOD OF USING THE SAME

(71) Applicants: Mahesh S. Mulumudi, Snohomish, WA (US); Ali F. Aboufares, New York, NY (US)

(72) Inventors: Mahesh S. Mulumudi, Snohomish, WA (US); Ali F. Aboufares, New York, NY (US)

(*) Notice: Subject to any disclaimer, the term of this patent is extended or adjusted under 35 U.S.C. 154(b) by 160 days.

This patent is subject to a terminal disclaimer.

(21) Appl. No.: 13/831,621

(22) Filed: Mar. 15, 2013

(65) Prior Publication Data

US 2013/0204346 A1 Aug. 8, 2013

Related U.S. Application Data

(63) Continuation of application No. 12/789,072, filed on May 27, 2010, now Pat. No. 8,439,962.

(60) Provisional application No. 61/181,859, filed on May 28, 2009.

(51) Int. Cl.

| | |
|---|---|
| *A61F 2/06* | (2013.01) |
| *A61F 2/958* | (2013.01) |
| *A61F 2/966* | (2013.01) |
| *A61F 2/97* | (2013.01) |
| *A61F 2/95* | (2013.01) |

(52) U.S. Cl.
CPC .................. *A61F 2/958* (2013.01); *A61F 2/966* (2013.01); *A61F 2/97* (2013.01); *A61F 2002/9517* (2013.01)
USPC ........................................................ 623/1.11

(58) Field of Classification Search
CPC ... A61F 2/95; A61F 2002/9517; A61F 2/966; A61F 2002/9665; A61F 2/97
USPC ........ 623/1.11, 1.23; 606/108, 191, 194, 198, 606/200; 128/898

See application file for complete search history.

(56) References Cited

U.S. PATENT DOCUMENTS

| | | |
|---|---|---|
| 5,921,956 A | 7/1999 | Grinberg et al. |
| 6,221,081 B1 | 4/2001 | Mikus et al. |
| 6,302,875 B1 | 10/2001 | Makower et al. |
| 6,395,017 B1 | 5/2002 | Dwyer et al. |
| 6,656,213 B2 | 12/2003 | Solem |
| 6,752,827 B2 | 6/2004 | Ross et al. |
| 6,830,575 B2 | 12/2004 | Stenzel et al. |
| 7,052,511 B2 | 5/2006 | Weldon et al. |
| 7,105,013 B2 | 9/2006 | Durcan |
| 7,125,419 B2 | 10/2006 | Sequin et al. |
| 7,766,953 B2 | 8/2010 | Purdy et al. |
| 7,803,137 B2 | 9/2010 | Stefanchik et al. |

(Continued)

OTHER PUBLICATIONS

International Search Report and Written Opinion, Application No. PCT/US10/36627, Dated Oct. 7, 2010.

(Continued)

*Primary Examiner* — Katherine M Shi
(74) *Attorney, Agent, or Firm* — Foley & Lardner LLP

(57) ABSTRACT

An endoprosthesis deployment system includes an axial catheter, an outer sheath extending parallel to the axial catheter, and an inner sheath positioned transversely between the axial catheter and outer sheath, the inner sheath including first and second inner sheath sections extending along the axial catheter, each of said first and said second inner sheath sections mounted for axial movement relative to the other inner sheath section.

15 Claims, 8 Drawing Sheets

(56) References Cited

U.S. PATENT DOCUMENTS

| | | |
|---|---|---|
| 2001/0014778 A1 | 8/2001 | Worm et al. |
| 2006/0085057 A1 | 4/2006 | George et al. |
| 2006/0184226 A1 | 8/2006 | Austin |
| 2008/0288042 A1 | 11/2008 | Purdy et al. |

OTHER PUBLICATIONS

US Notice of Allowance for U.S. Appl. No. 12/789,072 Dated Mar. 1, 2013.

US Office Action for U.S. Appl. No. 12/789,072 Dated Sep. 14, 2012.

ously between the axial catheter and outer sheath, the inner
ENDOPROSTHESIS STENT DELIVERY SYSTEM AND METHOD OF USING THE SAME This application is a continuation application of U.S. patent application Ser. No. 12/789,072, filed May 27, 2010, now U.S. Pat. No. 8,439,962, issued May 14, 2013, which claims the benefit of U.S. Provisional Patent App. Ser. No. 61/181,859, filed May 28, 2009.

BACKGROUND OF THE INVENTION

1. Field of the Invention

The present invention relates to an endoprosthesis stent delivery system and a method of using an endoprosthesis/stent delivery system, and particularly, to a system and method for deploying an endoprosthesis/stent within a hollow organ.

2. Discussion of the Related Art

In general, stent/endoprosthesis devices are placed within hollow organs, such as veins, arteries, esophagus, colon, and pancreatic tracts, to re-open or reinforce flow pathways through the hollow organs. One type of stent/endoprosthesis device is formed of a cylindrical wire mesh placed over an expandable balloon. Once the stent is delivered to the desired location, the balloon is inflated and expanded, thereby expanding the stent against interior sidewalls of the hollow organ. Then, the balloon is deflated and withdrawn from the hollow organ, thereby leaving the expanded stent within the hollow organ.

Another type of stent 1, as shown in FIG. 1, is formed of a self-expanding cylindrical wire mesh, but is compressed along an axial catheter 2 by a sheath 3 concentrically disposed about the axial catheter 2 before placement into a hollow organ 13 using a guide wire 4. The sheath assembly, which includes the axial catheter 2 and the sheath 3 with the compressed stent 1, is inserted into the hollow organ 13, and the compressed stent 1 is positioned at a targeted location P within the hollow the organ 13. Once the assembly is inserted into the hollow organ 13, and the axial catheter 2 and the compressed stent 1 are positioned at a targeted location P within the hollow organ 13, the sheath 3 is withdrawn along an axial length of the compressed stent 1 to allow for radial expansion of the stent 1 against the interior sidewall 15 of the hollow organ 13 due to the spring forces Fx and Fy of the compressed stent 1 along the x-axis and y-axis. However, precise placement of the stent 1 at targeted location P is difficult and the actual final positioning of the stem 1 is often unpredictable due to the spring forces Fx and Fy associated with the expansion of the stent 1. As a result, final location or position of the inner end of the stent 1 may be undesirably positioned a distance d from the target location P.

SUMMARY OF THE INVENTION

Accordingly, the present invention is directed to an endoprosthesis/stent delivery system, a method of using an endoprosthesis delivery system, and a method of deploying an endoprosthesis/stent device that substantially overcomes the disadvantages of the prior art.

In one aspect, an endoprosthesis deployment system includes an axial catheter, an outer sheath extending parallel to the axial catheter, and an inner sheath positioned transversely between the axial catheter and outer sheath, the inner sheath including first and second inner sheath sections extending along the axial catheter, each of said first and said second inner sheath sections mounted for axial movement relative to the other inner sheath section.

In another aspect, a method of deploying an endoprosthesis device within a hollow organ includes placing an axial catheter and inner sheath with an endoprosthesis device disposed therebetween at a first position within an interior of the hollow organ, the inner sheath including first and second inner sheath sections extending along an axial direction of the axial catheter, withdrawing the first inner sheath section along the axial direction to the second position to deploy a portion of the endoprosthesis device, and withdrawing the second inner sheath section along the axial direction to the second position to deploy a portion of the endoprosthesis device.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Reference will now be made in detail to the preferred embodiments of the present invention, examples of which are illustrated in the accompanying drawings.

Figure 1:
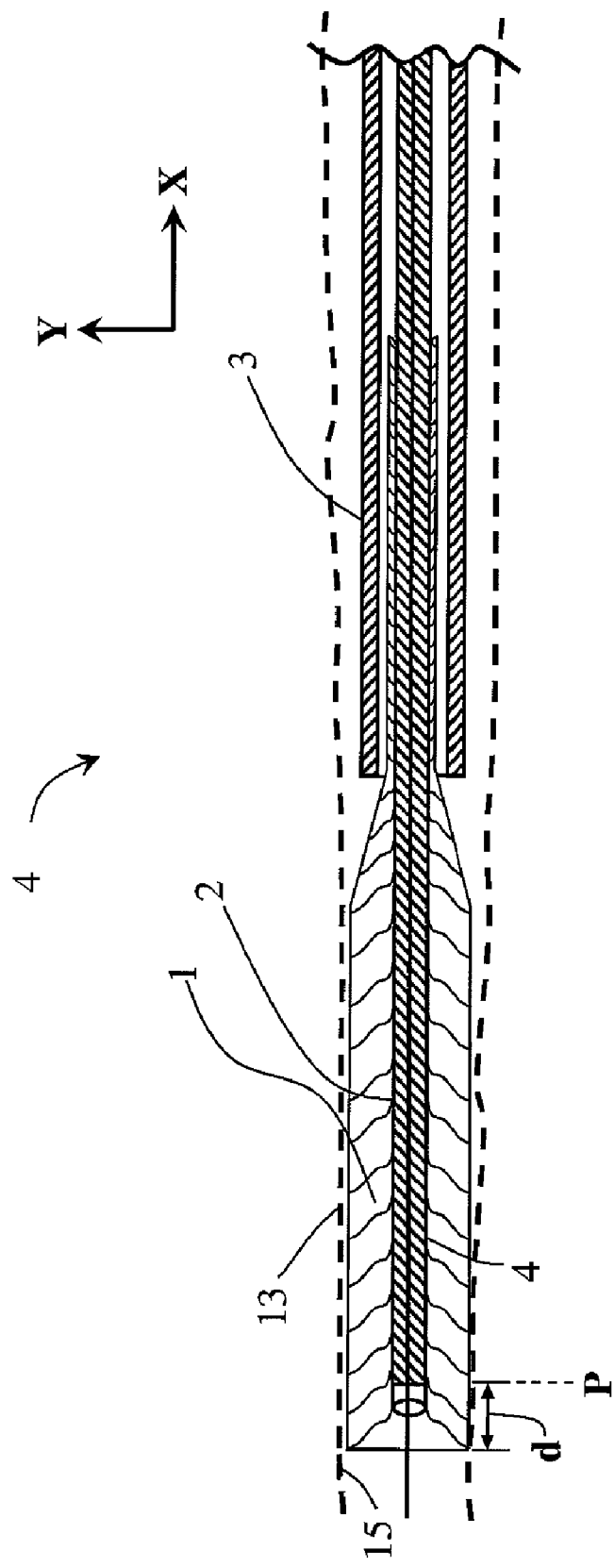
FIG. 1 is a schematic view of endoprosthesis delivery system according to the prior art.
Figure 2:
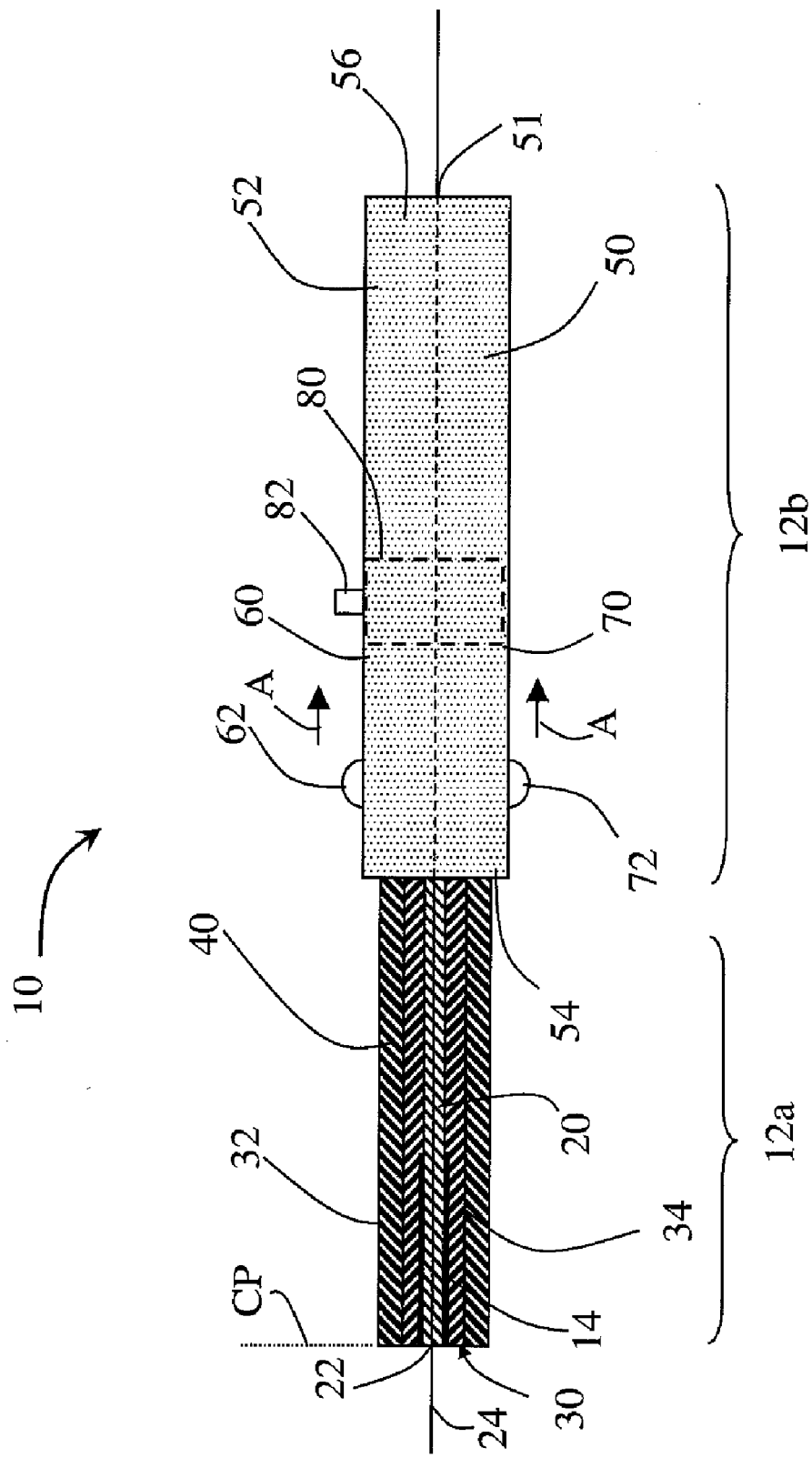
FIG. 2 is a schematic view of exemplary endoprosthesis delivery system according to the present invention.

As shown in FIG. 2, an endoprosthesis delivery system 10 generally includes functional components 12a and control components 12b. The functional components 12a include an axial catheter 20, an inner sheath 30, and an outer sheath 40, and the control components 12b include a deployment controller 50. Axial catheter 20 is generally formed having a substantially cylindrical geometry, but may possess other geometries, and includes a proximal portion disposed within the deployment controller 50 and a distal portion disposed at a distal end of the system 10 for insertion into a body. The axial catheter has a hollow axial passage 22 that travels along a guide wire 24 for guiding the delivery system 10 into a desired location in the body. The axial catheter 20 is attached to the deployment controller 50 such that the hollow axial passage 22 of the axial catheter 20 is continuous with a central hollow channel 51 in the controller 50. This central hollow channel 51 in the deployment controller 50 opens to a free end of a deployment controller housing or handle 52. The guide wire 24 over which the delivery system 10 travels to the desired location in the body, runs through the hollow axial passage 22 in the axial catheter 20 and through the central hollow channel 51 in the deployment controller 50 and exits out of the free end of the controller deployment housing 52.

According to one exemplary method for deploying a stent, the guide wire 24 is first placed into the body to the desired location, and then the delivery system 10 is threaded onto the guide wire 24 and inserted into the body to the desired location for deployment of a stent 14. Distal end surfaces of the outer sheath 40, the inner sheath 30, and the axial catheter 20 may be aligned to have a common end plane CP during insertion of the delivery system 10 into the body, as shown in FIG. 2. Outer sheath 40 is generally disposed concentrically about the inner sheath 30 and axial catheter 20. Therefore, outer sheath 40 extends axially or longitudinally to the proximal edge of the compressed stent. Although FIG. 2 shows the distal end surface of the outer sheath 40 being square, the end surface of the outer sheath 40 is actually tapered to prevent tearing of tissue walls during deployment of the functional components 12a of the delivery system 10. After deployment of the stent 14, as detailed below, the functional components 12a of the delivery system 10 are withdrawn from the body using the guide wire 24 as a track, and then the guide wire 24 is removed from the body.

Inner sheath 30 is generally disposed concentrically about the axial catheter 20, and includes a first inner sheath section 32 and a second inner sheath section 34, each having proximal portions operably disposed within the deployment controller 50 and distal portions movably disposed at the distal end of the delivery system 10. Within the deployment controller housing 52, the first and second inner sheath sections 32 and 34 of the inner sheath 30 are attached to control knobs 62 and 72 on either side of the deployment controller housing 52. The control knobs 62 and 72 can move independently. As discussed below, first inner sheath section 32 and second inner sheath section 34 are movably mounted for axial movement relative to one another so that one section can move while the other section is stationary or moving at a slower speed.

The proximal end of the outer sheath 40 is movably disposed within the deployment controller housing 52. The outer sheath 40 includes a channel extending therethrough which the assembly of first and second inner sheath sections 32 and 34 and the axial catheter 20 pass. The outer sheath 40 facilitates movement of the inner sheath 30 without interference from angulations and tortuosity rendered to the delivery system 10 from natural anatomy of the organ system being treated.

The deployment controller 50 includes the deployment controller housing 52 that houses various control mechanisms including first and second mechanisms 60 and 70 for controlling axial movement of the first and second inner sheath sections 32 and 34, respectively, and a third mechanism for controlling movement of the outer sheath 40. In addition, a fourth mechanism 80 is provided for controlling movement of the first and second mechanisms 60 and 70 within the deployment controller housing 52, as will be detailed below. At least two rack and pinion type mechanisms control movement of the first and second inner sheath sections 32 and 34 of the inner sheath 30 using the control knobs 62 and 72. These mechanisms can operate independently. One mechanism when rolled back moves one of the first and second inner sheath sections 32 and 34 of the inner sheath 30, and the second mechanism moves the other of the first and second inner sheath sections 32 and 34 of the inner sheath 30. Once the first and second inner sheath sections 32 and 34 move back independently to a certain distance to release the endoprosthesis/stent 14, both the mechanisms, if desired by the operator, can be moved back together to complete the deployment of the endoprosthesis/stent 14. Although not explicitly shown, the deployment controller 50 may also include other control mechanisms for controlling movement of other devices associated with deployment of endoprosthesis devices, as well as adjustments for associated electronic devices, i.e., video cameras and lighting.

The first mechanism 60 may include the control knob 62 for permuting a user to operate the first mechanism 60. In one embodiment, the first mechanism 60 is a rack and pinion mechanism and the control knob 62 functions as the pinion member while the rack member may be coupled to, or may be integral with, the proximal portion of the first inner sheath section 32. Alternatively, other mechanical, electromechanical, or hydraulic systems may used for controlling the first inner sheath section 32. The control knob 62 extends outwardly past an outer surface of the deployment controller housing 52 to allow a user to easily operate, e.g. slide in the direction A, the control knob 62 to control axial movement of the first inner sheath section 32. The corresponding rack member of the first mechanism 60 may reside within the deployment controller housing 52 and move along direction A. Alternatively, other control mechanisms may be provided to accomplish the function of controlling axial movement of the first inner sheath section 32. The first inner sheath section 32 of the inner sheath 30 is attached to the rack and pinion mechanism in such a way that the movement of the control knob 62 causes the movement of the first inner sheath section 32. The first inner sheath section 32 is attached to a slider (not shown) that would move back and forth with the movement of the control knob 62.

Similarly, the second mechanism 70 may be a rack and pinion mechanism, wherein a control knob 72 may function as the pinion member and the rack member may be coupled to, or may be integral with, the proximal portion of the second inner sheath 34. The control knob 72 extends outwardly past an outer surface of the deployment controller housing 52 to allow a user to easily manipulate the control knob 72 to control axial movement of the second inner sheath section 34. The corresponding rack member of the second mechanism 70 may reside within the deployment controller housing 52 and move along the direction A. Alternatively, other control mechanisms may be provided to accomplish the function of controlling axial movement of the second inner sheath section 34. For example, other mechanical, electromechanical, or hydraulic systems may used for controlling the second inner sheath section 34. The second inner sheath section 34 of the inner sheath 30 is attached to the rack and pinion mechanism in such a way that the movement of the control knob 72 causes the movement of the second inner sheath section 34. The second inner sheath section 34 is attached to a slider (not shown) that would move back and forth with the movement of the control knob 72.

For purposes of increased ergonomic efficiency and ease of operation, the first and second mechanisms 60 and 70 are provided at opposing sides of the deployment controller 50. Alternatively, the first and second mechanisms 60 and 70 may be provided at various locations and have various orientations with regard to a user's preference, such as for right-handed and left-handed users. In addition, placement of the first and second mechanisms 60 and 70 may be determined with regard to other control mechanisms of the endoprosthesis delivery system 10.

The fourth mechanism 80 may move the first and second mechanisms 60 and 70 synchronously together from a front portion 54 toward a rear portion 56 of the deployment controller housing 52. For example, each of the first and second mechanisms 60 and 70 may be disposed upon a moveable platform such that the fourth mechanism 80 may comprise a slide, or a rack and pinion, mechanism to accomplish the function of controlling synchronous movement of the first and second mechanisms 60 and 70. The first and second inner sheath sections 32 and 34 are attached to independent sliders (not shown) that can be moved back and forth by the rack and pinion mechanisms. The sliders for the first and second inner sheath sections 32 and 34 are attached together to the mechanism 80 that would engage once the rack and pinion knobs for the first and second inner sheath sections 32 and 34 roll back a certain distance. Once the mechanism 80 is engaged, the sliders for the first and second inner sheath sections 32 and 34 can be moved synchronously by operating the slider mechanism 80. The synchronous sliding mechanism 80 projects out of the deployment control housing 52 housing as a knob 82 that can slide in a channel in the deployment control housing 52.

Prior to insertion of the functional components 12a (in FIG. 2) into a hollow organ, the endoprosthesis delivery system 10 is assembled with an endoprosthesis device 14. For example, an endoprosthesis device 14 may be compressed and loaded onto the distal portion of the inner catheter 20 between the axial catheter 20 and distal portions of the first and second inner sheath sections 32 and 34. Alternatively, the endoprosthesis device may be loaded onto the functional components 12a (in FIG. 2) as a subassembly and separately joined to the deployment controller 50 to comprise the endoprosthesis delivery system 10. Independent of the method used to assemble and prepare the endoprosthesis delivery system 10 prior to insertion, the endoprosthesis device 14 is compressed along the axial direction of the axial catheter 20 between the axial catheter 20 and the first and second inner sheath sections 32 and 34. In addition, the outer sheath 40 is extended to cover the first and second inner sheath sections 32 and 34 for protection of the first and second inner sheath sections 32 and 34, as well as the compressed stent 14.

Figure 3:
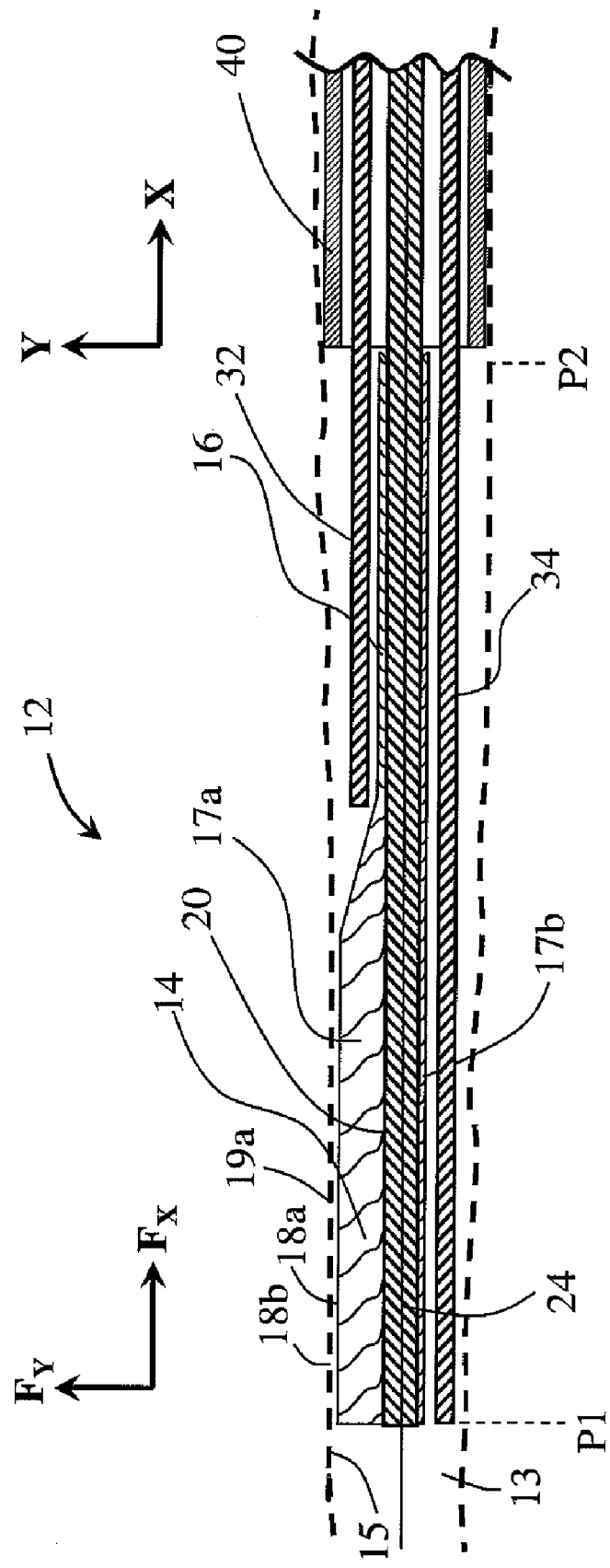
FIG. 3 is a schematic view of the exemplary endoprosthesis delivery system during a first deployment according to the present invention.

As shown in FIG. 3, once the functional components 12A of the endoprosthesis delivery system 10 (FIG. 2) are positioned at a first deployment position P1 within an interior of the hollow organ 13, the outer sheath 40 is withdrawn along an axial direction of the axial catheter 20 using the deployment controller 50 (FIG. 2) to a second deployment position P2 within the hollow organ 13. The second deployment position is past the proximal end of the stent 14. As a result, exterior surfaces of the first and second inner sheath sections 32 and 34 are exposed to interior sidewalls 15 of the hollow organ 13. In another embodiment, the outer sheath 40 may remain fixed relative to the deployment controller 50 (FIG. 2), and the axial catheter 20 and inner sheath 30 may be controlled to extend past the distal end of the outer sheath 40 from the common plane CP (FIG. 2) using control mechanisms (not shown) of the deployment control housing 52.

Next, the first inner sheath section 32 is retracted or withdrawn along the axial direction of the axial catheter 20 by the first mechanism 60 (FIG. 2) to deploy a first side portion 17a of the endoprosthesis device 14 to a position adjacent to a corresponding first side portion 19a of the interior sidewall 15 of the hollow organ 13. Specifically, the first inner sheath section 32 is withdrawn along the axial direction to deploy a first partial circumferential portion 18a of the endoprosthesis device 14 against a first partial circumferential interior sidewall portion 18b of the hollow organ 13. As the first inner sheath section 32 is further withdrawn to a third retracted or deployment position P3 (FIG. 4), an increasing length of the first partial circumferential portion 18a of the endoprosthesis device 14 is deployed along an increasing length of the first partial circumferential interior sidewall portion 18b of the hollow organ 13. In addition, a second side portion 17b of the endoprosthesis device 14 remains in the compressed state between the axial catheter 20 and the second inner sheath section 34. The second inner sheath section 34 also provides support to the device 14 and counteracts the spring or expansion threes of the expanding first side portion 17a to cause more controlled expansion. That is, by maintaining second inner sheath section 34 in a position supporting the device 14, second inner sheath section 34 minimizes axial spring forces (Fx) of the device 14 by maintaining contact and therefore frictional support, with device 14. As a result, as first inner sheath section 32 is withdrawn, second inner sheath section 34 permits precise deployment of the endoprosthesis device 14 within the hollow organ 13 by preventing the endoprosthesis device 14 from jumping/moving forward within the hollow organ 13.

Figure 4:
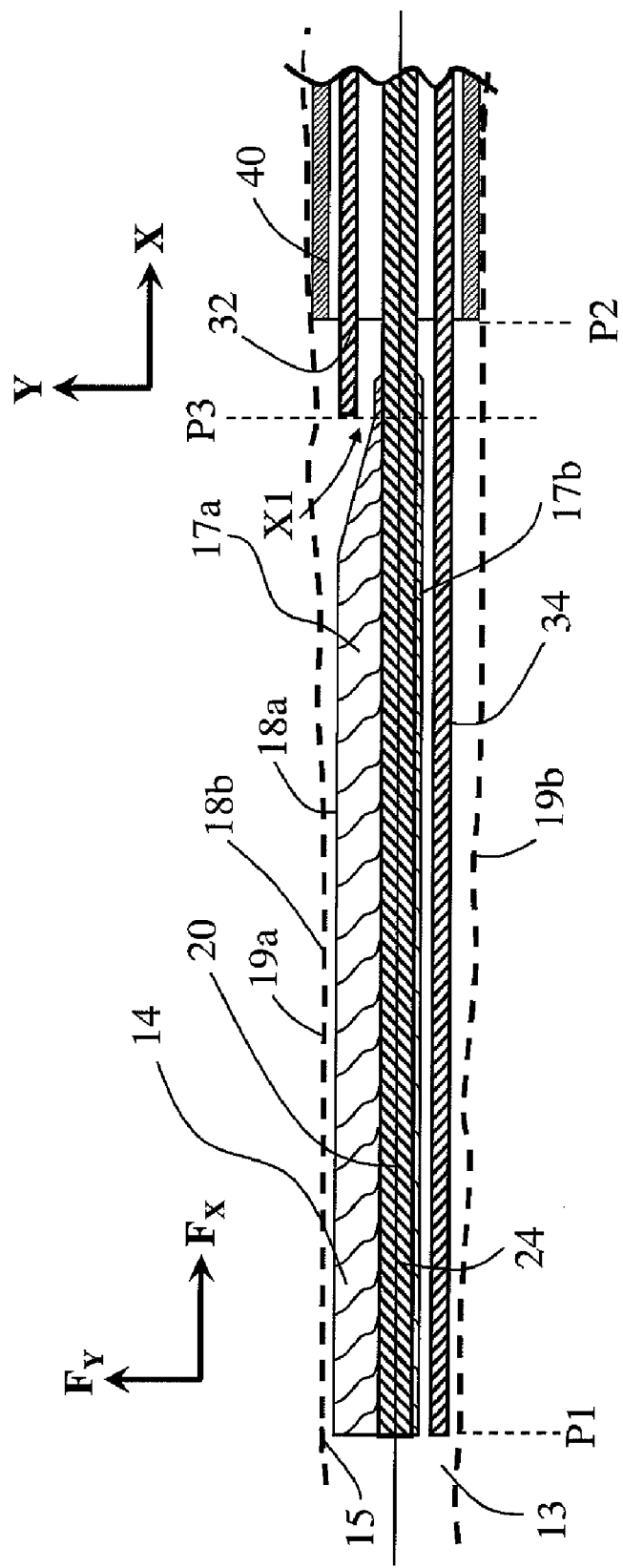
FIG. 4 is a schematic view of the exemplary endoprosthesis delivery system during a second deployment according to the present invention.

As shown in FIG. 4, once the first inner sheath section 32 has been withdrawn to the third deployment position P3, movement of the first inner sheath section 32 is stopped such that the first inner sheath section 32 overlaps a first end region X1 of the first side portion 17a of the endoprosthesis device 14. Accordingly, the first end region X1 of the endoprosthesis device 14 is not yet fully deployed against the corresponding first side portion 19a of the interior sidewall 15 of the hollow organ 13 in order to maintain relative placement of the endoprosthesis device 14. Moreover, the first deployment position P1 of the endoprosthesis device 14 may be confirmed, and may be adjusted if required, since a second side portion 17b of the endoprosthesis device 14 is still in the compressed state and not fully expanded against an opposing second side portion 19b of the interior sidewall 15 of the hollow organ 13. Once the first and second inner sheath sections 32 and 34 are moved back completely, no portions of the endoprosthesis device 14 remains compressed, so that device 14 is completely expanded within the hollow organ 13.

Figure 5:
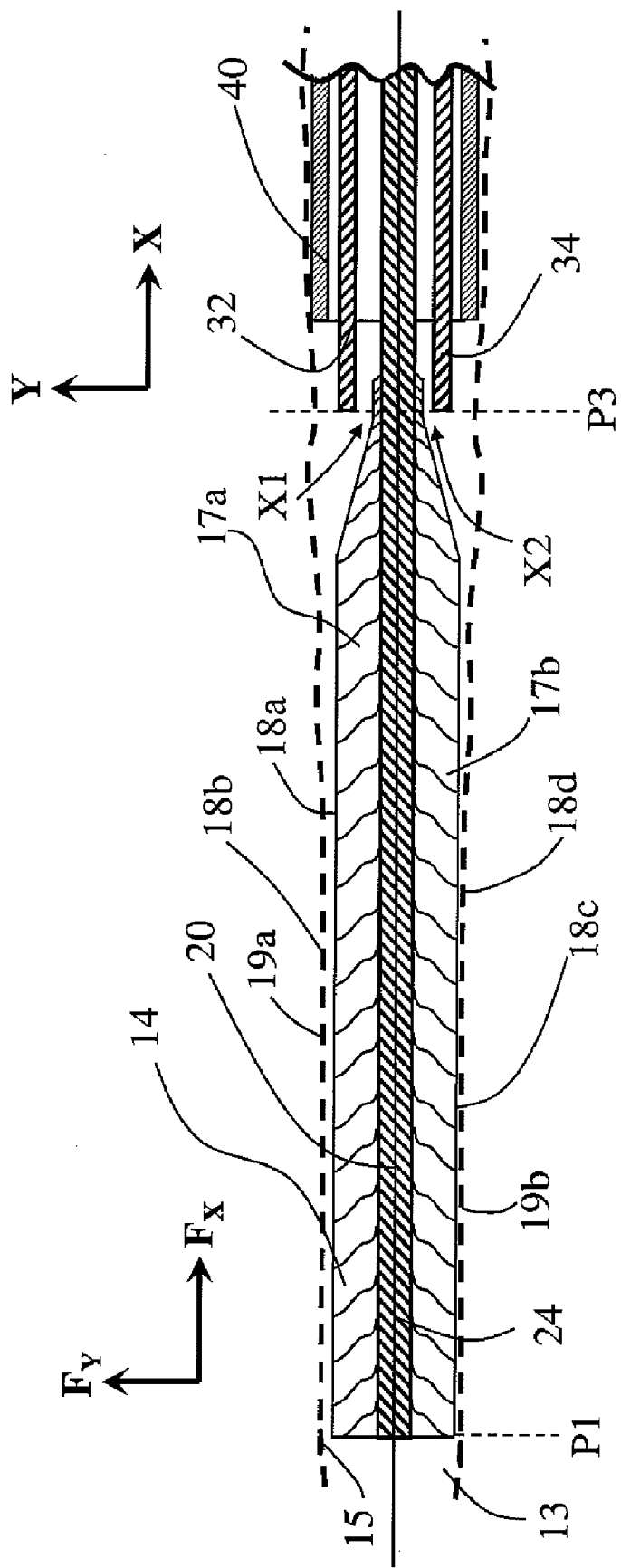
FIG. 5 is a schematic view of the exemplary endoprosthesis delivery system during a third deployment according to the present invention.

Next, as shown in FIG. 5, as the second inner sheath section 34 is withdrawn to the third deployment position P3, an increasing length of the second side portion 17b of the endoprosthesis device 14 is deployed along an increasing length of the second side portion 19b of the interior sidewall 15 of the hollow organ 13. Specifically, the second inner sheath section 34 is withdrawn along the axial direction to the third position P3 to deploy a second partial circumferential portion 18c of the endoprosthesis device 14 to a corresponding second partial circumferential interior sidewall portion 18d of the hollow organ 13. Once the second inner sheath section 34 has been withdrawn to the third deployment position P3, movement of the second inner sheath section 34 is stopped such that the second inner sheath section 34 overlaps a second end region X2 of the second side portion 19b of the endoprosthesis device 14. Accordingly, the first and second end regions X1 and X2 of the endoprosthesis device 14 are not yet be fully deployed against the corresponding first and second side portions 19a and 19b of the interior sidewall 15 of the hollow organ 13. It should be noted the retraction of second inner sheath section 34 may begin while inner sheath section 32 is still moving/retracting.

Figure 6:
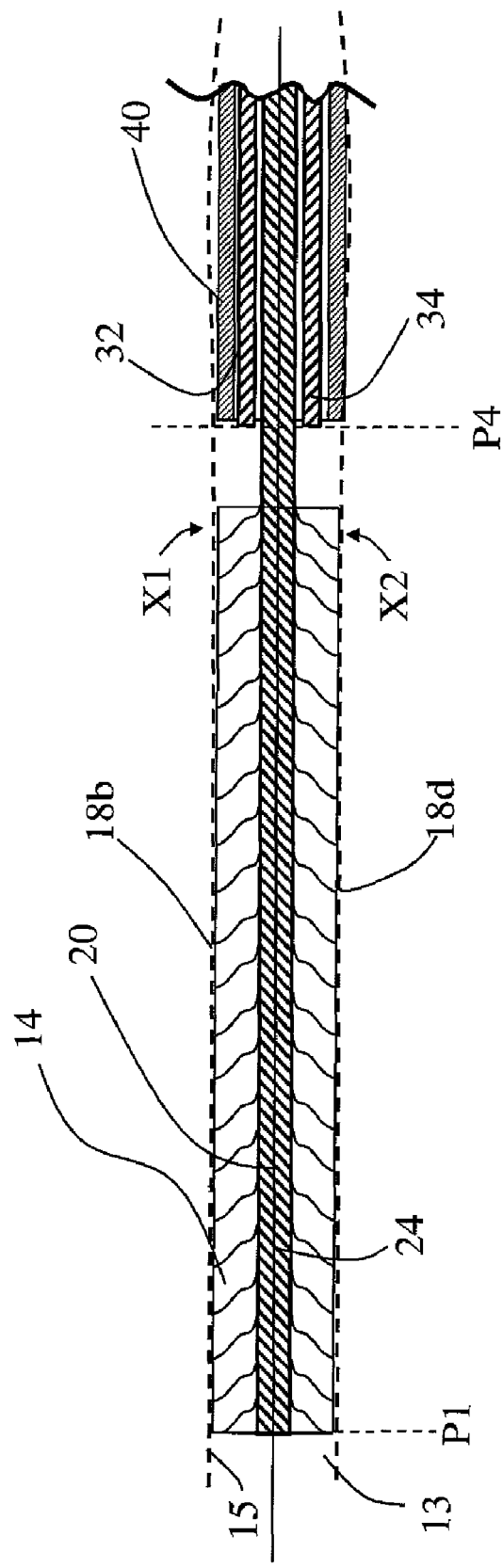
FIG. 6 is a schematic view of the exemplary endoprosthesis delivery system during a fourth deployment according to the present invention.

Finally, as shown in FIG. 2, the fourth mechanism 80 may be engaged to synchronously move the first and second mechanisms 60 and 70 toward the rear 56 of the deployment controller housing 52. As a result, as shown in FIG. 6, the first and second inner sheaths 32 and 34 may be further withdrawn along the axial direction of the inner catheter 20 to a fourth deployment position P4 where the distal ends of the first and second inner sheath sections 32 and 34 are spaced axially from the first and second end regions X1 and X2 of the endoprosthesis device 14. Thus, the first and second end regions X1 and X2 of the endoprosthesis device 14 may now be allowed to fully expand and be deployed against the corresponding first and second side portions 19a and 19b of the interior sidewall 15 of the hollow organ 13. This final deployment of the endoprosthesis device 14 allows for a substantially uniform expansion of the endoprosthesis device 14 against the interior sidewall 15 of hollow organ 13. In addition, the final deployment allows for the first and second inner sheath sections 32 and 34 to move synchronously to reduce the time of deployment and finger fatigue.

Figure 7A:
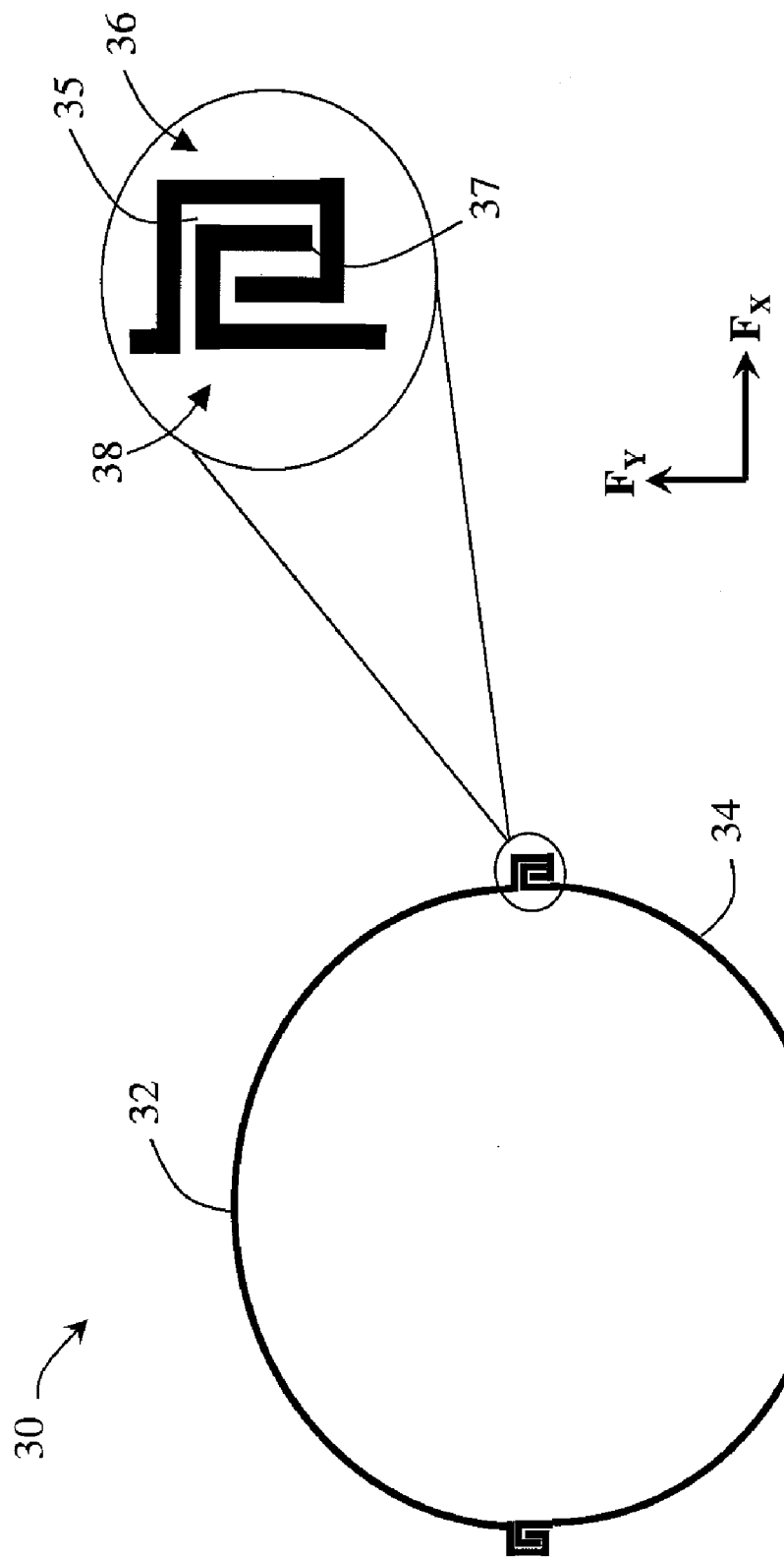
FIG. 7A is a cross-sectional view of a first exemplary inner sheath according to the present invention.
Figure 7B:
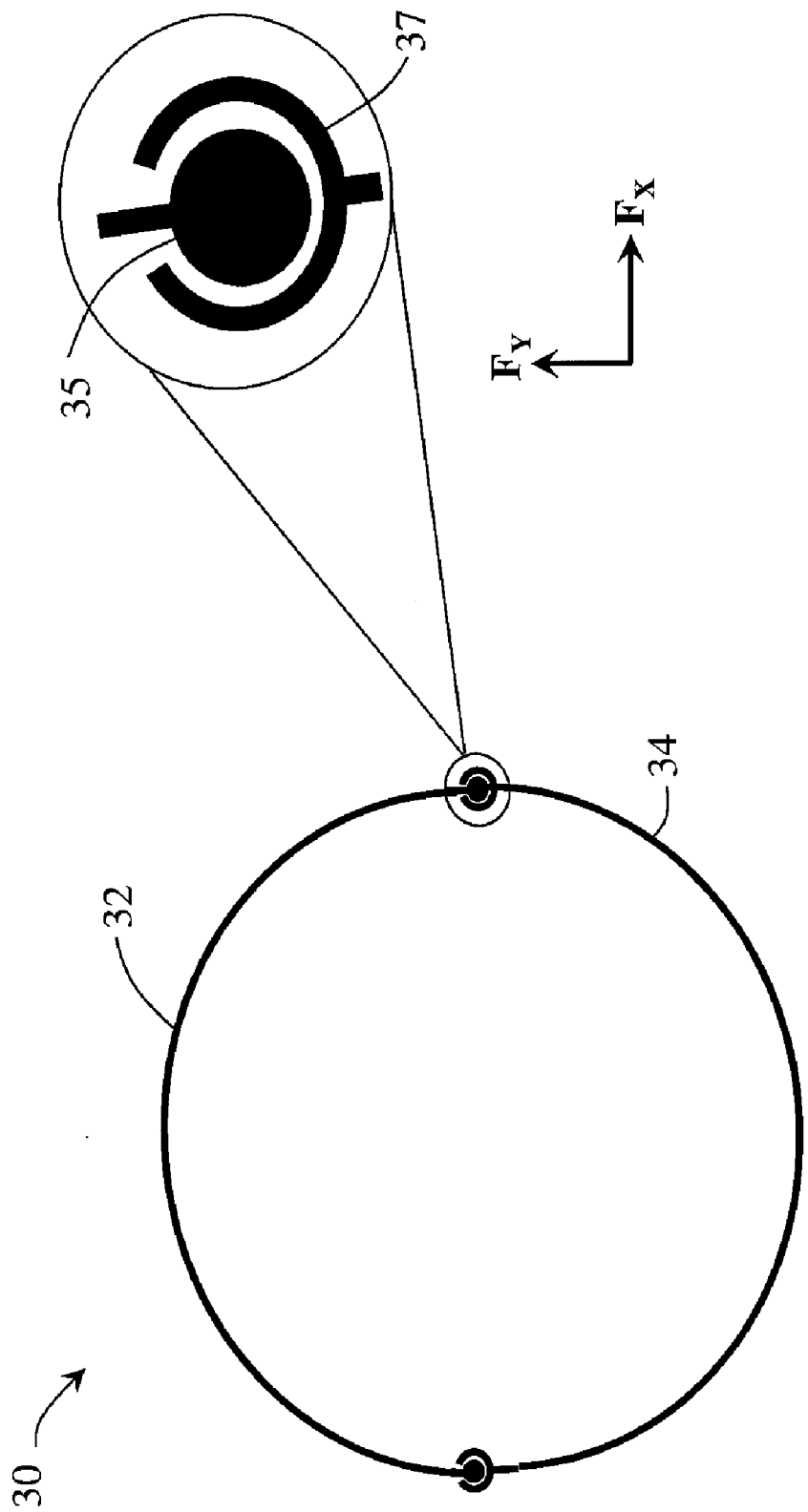
FIG. 7B is a cross-sectional view of a second exemplary inner sheath according to the present invention.

As shown in FIGS. 7A and 7B, the first and second inner sheath sections 32 and 34 are preferably axially coupled together along a length of the inner sheath 30. For example, as shown in FIG. 7A, a coupling system using rectilinear oriented flanges may be used. The coupling system includes a tongue and groove arrangement for permitting sliding between the first and second inner sheath sections 32 and 34. As shown in FIG. 7A, the tongue and groove arrangement may include a groove 35 formed by a first flange portion 36 formed on and extending axially along longitudinal edges of the first inner sheath section 32, and a tongue 37 formed by a second flange portion 38 formed on and extending axially along longitudinal edges of the second inner sheath section 34 opposite the first flange portion 36. The first flange portion 36 sandwiches the second flange portion 38 to create the connection. This connection may be formed with a relatively close fit between the first and second flange portions 36 and 38 to create an engagement or connection which resists inadvertent unintended relative axial sliding movement between the first and second inner sheath sections 32 and 34, but permits controlled relative sliding movement between the first and second inner sheath sections 32 and 34 upon the application of the appropriate axial operational force by a user. The first and second flange portions 36 and 38 form a connection that counteracts the spring forces Fx and Fy associated with the compressed forces of the endoprosthesis device 14 along the x-axis direction and the y-axis direction, respectively, during withdrawal of the first and second inner sheath sections 32 and 34.

As another example, as shown in FIG. 7B, a coupling system using a flange and channel arrangement is used. As shown in FIG. 7B, the flange and channel arrangement may include a flange portion 35 formed on and extending axially along longitudinal edges of the first inner sheath section 32 and a channel portion 37 formed on and extending axially along longitudinal edges of the second inner sheath section 34 opposite the flange portion 35. The channel portion 37 engages and retains the flange portion 35. A relatively close fit may be formed between the flange and channel portions 35 and 37 to create an engagement or connection which resists inadvertent unintended relative axial sliding movement or separation between the first and second inner sheath sections 32 and 34, but permits controlled relative axial sliding movement between the first and second inner sheath sections 32 and 34 upon the application of the appropriate axial operational force by a user. The flange and channel portions 35 and 37 form a connection that counteracts the spring forces Fx and Fy associated with the compressed forces of the endoprosthesis device 14 along the x-axis direction and the y-axis direction, respectively, during withdrawal of the first and second inner sheath sections 32 and 34.

The coupling systems, as shown in FIGS. 7A and 7B, provide for relative sliding of the first and second inner sheath sections 32 and 34, but prevent the distal ends of the first and second inner sheath sections 32 and 34 from being forced apart due to the compressed spring forces of the endoprosthesis device 14. That is, by using the coupling systems in FIGS. 7A and 7B, the first and second inner sheath sections 32 and 34 may be operated to slide along the axial direction of the axial catheter 20 to accurately deploy the endoprosthesis device 14, but prevent the first and second inner sheath sections 32 and 34 from opening up transversely outwardly in a jaw-like manner at the distal ends of the first and second inner sheath sections 32 and 34, as well as along the axial direction upon withdrawal of the first and second inner sheath sections 32 and 34. The coupling systems may extend along the entire length, or only a portion, of the longitudinal edges.

The inner sheath 30 may have a noncircular cross sectional shape such as an oblong shape, rectangular, etc. Whatever the outer shape of inner sheath 30, the first and second sheath sections may be of equal size or one section may comprise a greater extent of the shape. For example, the first inner sheath section 32 may have a cross-section having greater than 180 degrees of arc, and the second inner sheath section 34 may have a cross-section having less than 180 degrees of arc, or vice versa. In this case, the coupling systems may be disposed at locations other than directly opposing one another.

According to the present invention, the inner sheath 30 is formed having the first and second inner sheath sections 32 and 34. However, in some instances, the inner sheath 30 may formed having more than two inner sheath sections, such as three or more. For example, if the endoprosthesis device 14 is deployed within a body where different spring forces are required along length and/or radial directions, then the endoprosthesis device 14 would have corresponding non-homogeneous spring forces along its length and/or radial directions. Accordingly, the delivery system 10 may include three, four, or more inner sheath sections to accommodate for the different spring forces during deployment of the endoprosthesis within the body to ensure precise deployment at a desired location/position.

Moreover, combinations of multiple inner sheath sections with varying cross-sectional arcs may be used for precise deployment of an endoprosthesis device within a body. In addition, although the present invention is directed toward deployment within a hollow organ, the present invention may be used in other organs that may not necessarily be substantially hollow. For example, the present invention has applicability for placement of spacer-type devices within and between organs of the body, wherever precision deployment of medial devices is required.

According to the present invention, forming the inner sheath 30 having the first and second inner sheath sections 32 and 34, as well as providing independent control of the movement of first and second inner sheath sections 32 and 34, allows the endoprosthesis device 14 to be deployed within a hollow organ 13 in a much more controlled and precise manner rather than simply deploying an entire end of the endoprosthesis device 14 by releasing an entire circumference of the endoprosthesis device 14 against the interior sidewall of the hollow organ 13 by withdrawing a cylindrical inner sheath. Use of an inner sheath formed of first and second inner sheath sections 32 and 34 prevents the endoprosthesis device 14 from being propelled forward or jumping forward from a predetermined targeted deployment location due to full radial release of the compressed spring forces of the endoprosthesis device 14 without radial support of device 14 opposite the expanding portions of device 14.

According to the present invention, an endoprosthesis delivery system is capable of providing for accurate deployment of an endoprosthesis device within a hollow organ. By using an inner sheath comprising first and second inner sheath sections that are independently controllable to move along the axial direction of the axial catheter, the endoprosthesis device may be controllably released one sheath section at a time, e.g. sequentially, against interior sidewall of the hollow organ.

According to the present invention, coupling the first and second inner sheath sections using a coupling system having flanges formed longitudinally along edges of the first and second inner sheath sections creates an engagement or connection which resists inadvertent unintended relative radial movement or separation between the first and second inner sheath sections. At the same time, the coupling system permits controlled relative sliding movement between the first and second inner sheath sections by a user.

According to the present invention, a method of using an endoprosthesis delivery system provides for accurate deployment of an endoprosthesis device within a hollow organ. By providing a user with an ability to controllably release an endoprosthesis device one circumferential section at a time against interior sidewalls of the hollow organ, the endoprosthesis device may be deployed within a hollow organ in a much more controlled and precise manner rather than simply deploying an entire end of the endoprosthesis device by releasing an entire circumference of the endoprosthesis device against the interior sidewall of the hollow organ by withdrawing a cylindrical inner sheath. In addition, sequentially withdrawing first and second inner sheath sections along a length of the endoprosthesis device prevents the endoprosthesis device from being deployed in an incorrect position within the hollow organ by jumping forward due to rapid release of the compressed spring forces of the endoprosthesis device.

Although the present invention has been explained by the embodiments shown in the drawings described above, it should be understood to the ordinary skilled person in the art that the invention is not limited to the embodiments, but rather that various changes or modifications thereof are possible without departing from the spirit of the invention. Accordingly, the scope of the invention shall be determined only by the appended claims and their equivalents.

What is claimed is:

1. A stent delivery device comprising: a segmented sheath capable of overlying a radially expandable endoprosthesis stent with said stent being in a compressed condition; said segmented sheath capable of restraining said stent from radial expansion; and said segmented sheath comprising a plurality of adjacent flaps that in combination are capable of completely encircling said compressed stent, each of said flaps being axially slidable with respect to all other said flaps
    wherein a first of said flaps has a projection running along at least part of its length, and said projection is adapted to engage a corresponding structure on an adjacent second one of said flaps to form a slidable coupling configured to permit said first and second flaps to slide axially with respect to one another while restraining at least a portion of the stent from expanding radially; and
    wherein each of said first and second flaps has a longitudinal edge adjacent to the longitudinal edge of the other of said first and second flaps, and wherein said adjacent longitudinal edges are connected by said slidable coupling.

2. The device of claim 1, wherein each of said flaps has a deployment mechanism separate from the deployment mechanism of the other said flaps, and each of said deployment mechanisms is selected from the group consisting of (A) a rack and pinion mechanism and (B) a hydraulic mechanism.

3. The device of claim 1, wherein each of said flaps has a rack and pinion deployment mechanism separate from the rack and pinion deployment mechanism of the other said flaps, and including a mechanical linkage among said deployment mechanisms to permit the simultaneous movement of all of said flaps with respect to said stent.

4. The device of claim 1, wherein said corresponding structure is a track running along at least part of the length of said second one of said flaps.

5. The device of claim 4, wherein said projection has a bulbous cross-section and said track is a channel whose walls encircle said bulbous projection by more than 180 degrees.

6. The device of claim 4, in which said projection and said track both have hooked cross-sections that can be interlocked to form said slidable coupling.

7. The device of claim 4, wherein each of said flaps is joined to its adjacent flaps by said slidable couplings, said slidable couplings selected from the group consisting of (A) said projection having a bulbous cross-section and said track being a channel whose walls encircle said bulbous projection by more than 180 degrees, and (B) said projection and said track both having hooked cross-sections that can be interlocked to form said slidable coupling.

8. A method of deploying an endoprosthesis stent, said method comprising:
    providing a radially expandable endoprosthesis stent;
    restraining said stent in a compressed condition by completely encircling said stent with a segmented sheath that comprises a plurality of flaps, each of said flaps being axially slidable with respect to all other said flaps;
    providing a projection running along at least part of the length of said first of said flaps, said projection being adapted to engage a corresponding structure on an adjacent second one of said flaps to form a slidable coupling that is configured to permit said first and second flaps to slide axially with respect to one another while restraining at least a portion of the stent from expanding radially, wherein each of said first and second flaps has a longitudinal edge adjacent to the longitudinal edge of the other of said first and second flaps, and including providing said slidable coupling between said adjacent longitudinal edges;
    placing said sheath within a hollow organ with said stent radially compressed by said flaps; and,
    axially withdrawing a first of said flaps from overlying engagement with said compressed stent to a sufficient extent that at least a portion of said compressed stent radially decompresses in the region vacated by said withdrawn first flap.

9. The method of claim 8, further comprising providing each of said flaps with its own deployment mechanism, and including the step of withdrawing a second of said flaps from overlying engagement with said stent after said first flap has started being withdrawn from overlying engagement with said stent.

10. The method of claim 8, further comprising providing each of said flaps with its own deployment mechanism, and withdrawing a second of said flaps from overlying engagement with said stent at the same time as said first flap is withdrawn but at a different speed than said first flap is withdrawn.

11. The method of claim 8, further comprising providing each of said flaps with its own rack and pinion deployment mechanism, and also providing a mechanical linkage among said deployment mechanisms to permit the simultaneous movement of all of said flaps with respect to said stent, and including the step of withdrawing all of said flaps from said stent simultaneously at the same speed.

12. The method of claim 8, wherein said corresponding structure is a track running along at least part of the length of said second one of said flaps.

13. The method of claim 12, wherein said projection has a bulbous cross-section and said track is a channel whose walls encircle said bulbous projection by more than 180 degrees.

14. The method of claim 12, wherein said projection and said track both have hooked cross-sections and including the step of interlocking said projection and said track to form said slidable coupling.

15. The method of claim 12, wherein each of said flaps is joined to its adjacent flaps by said slidable couplings, and selecting said slidable couplings from the group consisting of (A) said projection having a bulbous cross-section and said track being a channel whose walls encircle said bulbous projection by more than 180 degrees, and (B) said projection and said track both having hooked cross-sections; and including the step of interlocking said projection and said track to form said slidable coupling.

* * * * *